United States Patent
Denny et al.

(10) Patent No.: US 8,012,764 B2
(45) Date of Patent: Sep. 6, 2011

(54) MASS SPECTROMETER

(75) Inventors: Richard Denny, Newcastle-unde-Lyme (GB); Keith Richardson, High peak (GB); John Skilling, Country Kerry (IE)

(73) Assignee: Micromass UK Limited, Manchester (GB)

(*) Notice: Subject to any disclaimer, the term of this patent is extended or adjusted under 35 U.S.C. 154(b) by 921 days.

(21) Appl. No.: 11/568,408

(22) PCT Filed: May 3, 2005

(86) PCT No.: PCT/GB2005/001679
§ 371 (c)(1),
(2), (4) Date: Dec. 10, 2007

(87) PCT Pub. No.: WO2005/106453
PCT Pub. Date: Nov. 10, 2005

(65) Prior Publication Data
US 2008/0076186 A1 Mar. 27, 2008

(30) Foreign Application Priority Data

Apr. 30, 2004 (GB) .................................. 0409677.2
May 20, 2004 (GB) .................................. 0411248.8

(51) Int. Cl.
*G01N 35/00* (2006.01)
*G01N 24/00* (2006.01)

(52) U.S. Cl. ............ 436/173; 436/43; 436/63; 436/149; 436/86; 436/174

(58) Field of Classification Search ............ 436/43, 436/63, 149, 86, 174, 173
See application file for complete search history.

(56) References Cited

U.S. PATENT DOCUMENTS

| | | | | |
|---|---|---|---|---|
| 5,087,815 A * | 2/1992 | Schultz et al. | ................. | 850/63 |
| 5,545,894 A * | 8/1996 | Funsten et al. | ................. | 250/281 |
| 5,679,950 A * | 10/1997 | Baba et al. | ..................... | 250/281 |
| 5,910,655 A | 6/1999 | Skilling | | |
| 6,393,367 B1 * | 5/2002 | Tang et al. | ....................... | 702/19 |
| 6,446,010 B1 * | 9/2002 | Eriksson et al. | ................. | 702/19 |
| 6,489,608 B1 * | 12/2002 | Skilling | ....................... | 250/281 |
| 6,556,651 B1 * | 4/2003 | Thomson et al. | ................. | 378/65 |
| 2002/0053545 A1 | 5/2002 | Greef | | |
| 2002/0192720 A1 | 12/2002 | Parker et al. | | |

(Continued)

FOREIGN PATENT DOCUMENTS
EP 1319954 6/2003
(Continued)

OTHER PUBLICATIONS

Kang et al. "Radical detection in a methane plasma," J. Vac. Sci. Technol. A 21(6), Nov./Dec. 2003; vol. 21, No. 6, pp. 1978-1980; publication date: Oct. 15, 2003.*

(Continued)

*Primary Examiner* — Brian J Sines
(74) *Attorney, Agent, or Firm* — Waters Technologies Corp

(57) ABSTRACT

A mass spectrometer and method of mass spectrometry are disclosed wherein two separate samples are mass analysed and then the relative intensity, concentration or expression level of one or more components, molecules or analytes in a first sample is quantitated relative to the intensity, concentration or expression level of one or more components, molecules or analytes in a second sample. The relative quantitation is performed probabilistically without the need to resort to using internal calibrants.

26 Claims, 2 Drawing Sheets

| | | Sample 1 | | Sample 2 | | Sample 3 | | Sample 4 | |
|---|---|---|---|---|---|---|---|---|---|
| | | Expt 1 | Expt 2 | Expt 3 | Expt 4 | Expt 5 | Expt 6 | Expt 7 | Expt 8 |
| Internal Std. | Dau 1 | 28730 | 13950 | 59950 | 19890 | 12260 | | 11970 | 7800 |
| | Dau 2 | 449880 | | 946590 | 320800 | 195370 | | | |
| | Dau 3 | 22420 | 10760 | 46300 | 15820 | | | 8080 | 5820 |
| | | | | | | | | | |
| Analyte 1. | Dau 1 | 34360 | 16960 | 509810 | | | 9770 | 47400 | 33230 |
| | Dau 2 | 1640 | | 25940 | 9320 | 930 | 450 | 2310 | |
| | Dau 3 | 30650 | 15490 | 466860 | 157820 | 18860 | 8800 | 43070 | 30650 |

U.S. PATENT DOCUMENTS

| | | | |
|---|---|---|---|
| 2003/0052264 A1* | 3/2003 | Baba et al. | 250/281 |
| 2003/0077840 A1 | 4/2003 | Chait et al. | |
| 2003/0111596 A1 | 6/2003 | Becker et al. | |
| 2006/0003460 A1* | 1/2006 | Appel et al. | 436/86 |
| 2006/0234326 A1* | 10/2006 | Cerda | 435/15 |
| 2008/0138909 A1* | 6/2008 | Wheeler et al. | 436/89 |
| 2008/0185516 A1* | 8/2008 | Baba et al. | 250/288 |
| 2009/0057550 A1* | 3/2009 | Stults et al. | 250/282 |

FOREIGN PATENT DOCUMENTS

| | | | |
|---|---|---|---|
| GB | 2391699 | | 2/2004 |
| GB | 2394545 | * | 4/2004 |
| WO | WO02/086168 | | 10/2002 |
| WO | WO03/098182 | | 11/2003 |

OTHER PUBLICATIONS

Preuss et al. ("Quantitative Analysis of Multicomponent Mass Spectra," AIP Conf. Proc. USA No. 617, pp. 155-162 (2002).*

Hellerstein et al., "Mass Isotopomer Distribution Analysis at Eight Years: Theoretical, Analytic, and Experimental Considerations", American Journal of Physiology: Endocrinology and Metabolism, American Physiological Society, vol. 276, No. 39, 1999, pp. E1146-E1170.

* cited by examiner

|  | Sample 1 | | Sample 2 | | Sample 3 | | Sample 4 | |
|---|---|---|---|---|---|---|---|---|
|  | Expt 1 | Expt 2 | Expt 3 | Expt 4 | Expt 5 | Expt 6 | Expt 7 | Expt 8 |
| Internal Std. Day 1 | 28730 | 13950 | 59950 | 19890 | 12260 |  | 11970 | 7800 |
| Internal Std. Day 2 | 449880 |  | 946590 | 320800 | 195370 |  |  |  |
| Internal Std. Day 3 | 22420 | 10760 | 46300 | 15820 |  |  | 8080 | 5820 |
| Analyte 1. Day 1 | 34360 | 16960 | 509810 |  |  | 9770 | 47400 | 33230 |
| Analyte 1. Day 2 | 1640 |  | 25940 | 9320 | 930 | 450 | 2310 |  |
| Analyte 1. Day 3 | 30650 | 15490 | 466860 | 157820 | 18860 | 8800 | 43070 | 30650 |

FIG. 1

| Parameters h | h1/h1 | h2/h1 | h3/h1 | h4/h1 | h5/h1 | h6/h1 | h7/h1 | h8/h1 |
|---|---|---|---|---|---|---|---|---|
| Actual | 1 | 0.48 | 2.09 | 0.71 | 0.43 | 0.2 | 0.39 | 0.28 |
| Quantify | 1 | 0.49 | 2.1 | 0.71 | 0.43 | 0.2 | 0.39 | 0.27 |

| Parameters L | L2/L1 | L3/L1 | L4/L1 | L3/L2 | L4/L2 | L4/L3 |
|---|---|---|---|---|---|---|
| Actual | 7.12 | 1.43 | 3.53 | 0.2 | 0.5 | 2.46 |
| Quantify | 7.13+/-0.09 | 1.39+/-0.04 | 3.56+/-0.08 | 0.20+/-0.00 | 0.5+/-0.01 | 2.56+/-0.08 |

FIG. 2

MASS SPECTROMETER

CROSS REFERENCE TO RELATED APPLICATIONS

This application is the National Stage of International Application No. PCT/GB05/01679, filed on May 3, 2005, which claims priority to and benefit of United Kingdom Patent Application No. 0409677, filed Apr. 30, 2004, and United Kingdom Patent Application No. 0411248, filed May 20, 2004. The entire contents of these applications are incorporated herein by reference.

BACKGROUND OF THE INVENTION

The present invention relates to a method of mass spectrometry and a mass spectrometer. The preferred embodiment relates to a method which allows relative quantitation of analyte compounds especially where incomplete and noisy measurements are made. The preferred embodiment is particularly applicable to the measurement and quantitation of peptide digest products or daughter compound abundances. The preferred embodiment relates to relative Bayesian quantitation of analyte/daughter groups.

As will be discussed in more detail below, the preferred embodiment relates to a probabilistic or Bayesian approach to determining the relative quantitation of a component, molecule or analyte present in two or more samples. By way of background, Bayesian probability theory handles probabilities of statements. Probabilities tell how certain those statements are true. For example, a probability of 1 means that there is absolute certainty. A probability of 0 also means that there is absolute certainty, but absolute certainty that the statement is false. A probability of 0.5 means that there is maximum uncertainty whether the statement is true or false.

Changing probabilities when getting new information is an important aspect of Bayesian reasoning. So called Bayes rule defines how a rational agent changes its beliefs when it gets new information (evidence).

Bayesian probabilities or certainties are always conditional. This means that probabilities are estimated in the context of some background assumptions. Conditional probabilities are usually written using the notation P(Thing|Assumption). The probabilities are numbers between zero and one that tell how certain it is that Thing is true when it is believed that the Assumption is true. Conditional probabilities are often written in the form P(D|M) or P(M|D), where M is dependency model and D is data. Accordingly, P(D|M) means the probability of obtaining data D if it is believed that model M is the true model. Likewise, P(M|D) means the probability that the model M is the true model given the data D. Sometimes probabilities are presented just as P(M) or P(D) but these are generally considered to be imprecise Bayesian notations, since all the probabilities are actually conditional. However, sometimes, when all the terms have the same background assumptions then it may not be necessary to repeat them. In theory, probabilities should be written in the form P(D|M,U) and P(M|D,U) and P(M|U) and P(D|U), where U is a set of background assumptions.

Expert systems often calculate the probabilities of interdependent events by giving each parent event a weighting. Bayesian Belief Networks are considered to provide a mathematically correct and therefore more accurate method of measuring the effects of events on each other. The mathematics involved enables calculations to be made in both directions. So it is possible, for example, to find out which event was the most likely cause of another.

The following Product Rule of probability for independent events is well known:

$$p(AB)=p(A)*p(B)$$

where p(AB) means the probability of A and B happening.

This is a special case of the following Product Rule for dependent events, where p(A|B) means the probability of A given that B has already occurred:

$$p(AB)=p(A)*p(B|A)$$

$$p(AB)=p(B)*p(A|B)$$

So because:

$$p(A)p(B|A)=p(B)p(A|B)$$

Then:

$$p(A|B)=(p(A)*p(B|A))/p(B)$$

The above equation is a simpler version of Bayes' Theorem. This equation gives the probability of A happening given that B has happened, calculated in terms of other probabilities which are known.

Bayes' theorem can be summarised as:

$$P(H_0 \mid E) = \frac{P(E \mid H_0)P(H_0)}{P(E)}$$

$H_0$ can be taken to be a hypothesis which may have been developed ab initio or induced from some preceding set of observations, but before the new observation or evidence E. The term $P(H_0)$ is called the prior probability of $H_0$. The term $P(E|H_0)$ is the conditional probability of seeing the observation E given that the hypothesis $H_0$ is true—as a function of $H_0$ given E, it is called the likelihood function. The term P(E) is called the marginal probability of E and it is a normalizing constant and can be calculated as the sum of all mutually exclusive hypotheses:

$$\Sigma P(E|H_i)P(H_i)$$

The term $P(H_0|E)$ is called the posterior probability of $H_0$ given E. The scaling factor $P(E|H_0)/P(E)$ gives a measure of the impact that the observation has on belief in the hypothesis. If it is unlikely that the observation will be made unless the particular hypothesis being considered is true, then this scaling factor will be large. Multiplying this scaling factor by the prior probability of the hypothesis being correct gives a measure of the posterior probability of the hypothesis being correct given the observation.

The keys to making the inference work is the assigning of the prior probabilities given to the hypothesis and possible alternatives, and the calculation of the conditional probabilities of the observation under different hypotheses.

In the analysis of multiple biological samples or a complex mixture of biological samples it may be desired to compare the relative concentrations of component compounds. For example, it may be desired to see whether or not a protein or peptide is expressed differently in two or more different samples. One sample may, for example, comprise a sample taken from a healthy organism, whilst the other sample may comprise a sample taken from a patient. If a particular protein or peptide is expressed to a significantly greater or lesser extent in the patient sample relative to the sample taken from a healthy organism (i.e. control sample) then this may be indicative of a disease state.

Complex mixtures of biological samples can be analysed using a mass spectrometer preferably in combination with a liquid chromatograph.

It is known to use the ion intensity or ion count rate recorded by a mass spectrometer as a measure of the concentration of each peptide. The data relating to each sample is, however, subject to various systematic errors such as injection volume errors as well as various non-systematic effects such as counting statistics.

Due to the complexity of the samples and the sometimes low concentrations of various components, molecules or analytes in the samples, the data can sometimes or often be incomplete. The data may also include interferences. As a result the assignment of data to components, molecules or analytes or the identification of components, molecules or analytes may be uncertain.

According to conventional approaches these factors can cause results that may appear to be anomalous and hence are thus discarded. As a result, it may not always be possible to quantify some components, molecules or analytes present in two or more samples and/or some data may be rejected out of hand when in fact it may not be anomalous.

It is therefore desired to provide an improved way of being able to quantify components, molecules or analytes present in two or more separate samples when noisy and incomplete measurements of the samples are made.

SUMMARY OF THE INVENTION

According to an aspect of the present invention there is provided a method of mass spectrometry comprising:

providing a first sample comprising a first mixture of components, molecules or analytes;

providing a second different sample comprising a second mixture of components, molecules or analytes; and probabilistically determining or quantifying the relative intensity, concentration or expression level of a component, molecule or analyte in the first sample relative to the intensity, concentration or expression level of a component, molecule or analyte in the second sample.

Although the preferred embodiment may just relate to two separate samples, according to a particularly preferred embodiment a plurality of further samples each comprising a mixture of components, molecules or analytes may be provided. The components, molecules or analytes preferably comprise proteins, protein digest products, peptides or fragments of peptides.

The components, molecules or analytes in the first mixture are preferably the same species as the components, molecules or analytes in the second mixture and/or components, molecules or analytes in further mixtures. However, alternatively, the components, molecules or analytes in the first mixture may be different species to the components, molecules or analytes in the second mixture and/or to components, molecules or analytes in further mixtures.

The method preferably further comprises: digesting the first mixture of components, molecules or analytes; and/or digesting the second mixture of components, molecules or analytes; and/or digesting further mixtures of components, molecules or analytes. Preferably, the first mixture of components, molecules or analytes is digested to form a first complex mixture; and/or the second mixture of components, molecules or analytes is digested to form a second complex mixture; and/or further mixtures of components, molecules or analytes are digested to form further complex mixtures.

The complex mixtures preferably comprise complex mixtures of peptides or protein digest products.

According to the preferred embodiment the method further comprises: dividing the first sample into one or more first replicate samples; and/or dividing the second sample into one or more second replicate samples; and/or dividing further samples into one or more further replicate samples; and/or dividing the first complex mixture into one or more first replicate samples; and/or dividing the second complex mixture into one or more second replicate samples; and/or dividing the further complex mixtures into one or more further replicate samples.

According to an embodiment the method further comprises: separating components, analytes or molecules in the first sample by means of a separation process; and/or separating components, analytes or molecules in the second sample by means of a separation process; and/or separating components, analytes or molecules in further samples by means of a separation process; and/or separating components, analytes or molecules in the first replicate samples by means of a separation process; and/or separating components, analytes or molecules in the second replicate samples by means of a separation process; and/or separating components, analytes or molecules in further replicate samples by means of a separation process.

The separation process preferably comprises liquid chromatography. According to an embodiment the separation process may comprise: (i) High Performance Liquid Chromatography ("HPLC"); (ii) anion exchange; (iii) anion exchange chromatography; (iv) cation exchange; (v) cation exchange chromatography; (vi) ion pair reversed-phase chromatography; (vii) chromatography; (viii) single dimensional electrophoresis; (ix) multi-dimensional electrophoresis; (x) size exclusion; (xi) affinity; (xii) revere phase chromatography; (xiii) Capillary Electrophoresis Chromatography ("CEC"); (xiv) electrophoresis; (xv) ion mobility separation; (xvi) Field Asymmetric Ion Mobility Separation or Spectrometry ("FAIMS"); or (xvi) capillary electrophoresis.

The method preferably further comprises: ionising components, analytes or molecules in the first sample; and/or ionising components, analytes or molecules in the second sample; and/or ionising components, analytes or molecules in further samples; and/or ionising components, analytes or molecules in the first replicate samples; and/or ionising components, analytes or molecules in the second replicate samples; and/or ionising components, analytes or molecules in further replicate samples.

The method preferably further comprises: mass analysing components, analytes or molecules in the first sample; and/or mass analysing components, analytes or molecules in the second sample; and/or mass analysing components, analytes or molecules in further samples; and/or mass analysing components, analytes or molecules in the first replicate samples; and/or mass analysing components, analytes or molecules in the second replicate samples; and/or mass analysing components, analytes or molecules in further replicate samples.

The step of mass analysing components, analytes or molecules preferably further comprises producing mass spectral data comprising a plurality of mass peaks. Preferably, the method further comprises determining the mass or mass to charge ratio of one or more of the mass peaks. Preferably, the method further comprises determining the signal intensity, or the integrated signal, for one or more of the mass peaks.

According to the preferred embodiment the method further comprises determining the retention time for one or more of the mass peaks.

Preferably, the method further comprises clustering mass peaks from the first sample and/or the second sample and/or further samples. Preferably, the method comprises clustering mass peaks from the first replicate sample and/or the second replicate sample and/or further replicate samples.

According to an embodiment the method further comprises: recognising or identifying components, analytes or molecules in the first sample; and/or recognising or identifying components, analytes or molecules in the second sample; and/or recognising or identifying components, analytes or molecules in further samples; and/or recognising or identifying components, analytes or molecules in the first replicate samples; and/or recognising or identifying components, analytes or molecules in the second replicate samples; and/or recognising or identifying components, analytes or molecules in further replicate samples.

The components, analytes or molecules are preferably recognised or identified on the basis of mass or mass to charge ratio or accurate mass or accurate mass to charge ratio. The accurate mass or mass to charge ratio of the components, analytes or molecules is preferably determined to within 20 ppm, 19 ppm, 18 ppm, 17 ppm, 16 ppm, 15 ppm, 14 ppm, 13 ppm, 12 ppm, 11 ppm, 10 ppm, 9 ppm, 8 ppm, 7 ppm, 6 ppm, 5 ppm, 4 ppm, 3 ppm, 2 ppm, 1 ppm or <1 ppm.

The mass or mass to charge ratio of the components, analytes or molecules is preferably determined to within 0.01 mass units, 0.009 mass units, 0.008 mass units, 0.007 mass units, 0.006 mass units, 0.005 mass units, 0.004 mass units, 0.003 mass units, 0.002 mass units, 0.001 mass units or <0.001 mass units.

Components, analytes or molecules are preferably recognised or identified on the basis of chromatographic retention time or another physico-chemical property.

According to an embodiment, the method further comprises fragmenting components, molecules or analytes in a collision or fragmentation cell to form, create or generate a plurality of fragment, daughter or product ions. Preferably, the fragment, daughter or product ions are mass analysed.

According to an embodiment the method further comprises: identifying or recognising components, molecules or analytes in the first sample on the basis of fragment, daughter or product ions; and/or identifying or recognising components, molecules or analytes in the second sample on the basis of fragment, daughter or product ions; and/or identifying or recognising components, molecules or analytes in further samples on the basis of fragment, daughter or product ions.

According to an embodiment the method further comprises obtaining or assigning probabilities for the correct identification of mass peaks. Preferably, the method further comprises determining or deriving the probabilities from a protein search procedure.

The method preferably further comprises assigning a constant probability of correct identification where no probability is determined or derived from a protein search procedure. Preferably, the method further comprises assigning the probability of correct identification as a value x% wherein preferably x is selected from the group consisting of: (i)<5%; (ii) 5-10%; (iii) 10-15%; (iv) 15-20%; (v) 20-25%; (vi) 25-30%; (vii) 30-35%; (viii) 35-40%; (ix) 40-45%; (x) 45-50%; (xi) 50-55%; (xii) 55-60%; (xiii) 60-65%; (xiv) 65-70%; (xv) 70-75%; (xvi) 75-80%; (xvii) 80-85%; (xviii) 85-90%; (xix) 90-95%; and (xx)>95%.

According to an embodiment the method further comprises assigning a constant probability of correct identification in the event that no protein search procedure is performed. Preferably, the method further comprises assigning the probability of correct identification as a value x%.

Preferably, x is selected from the group consisting of: (i)<5%; (ii) 5-10%; (iii) 10-15%; (iv) 15-20%; (v) 20-25%; (vi) 25-30%; (vii) 30-35%; (viii) 35-40%; (ix) 40-45%; (x) 45-50%; (xi) 50-55%; (xii) 55-60%; (xiii) 60-65%; (xiv) 65-70%; (xv) 70-75%; (xvi) 75-80%; (xvii) 80-85%; (xviii) 85-90%; (xix) 90-95%; and (xx)>95%.

According to an embodiment the method further comprises determining, formulating or assigning a prior probability distribution function $Pr(L)$ for the relative amount or concentration L of components, molecules or analytes present in each sample. Preferably, the prior probability distribution function $Pr(L)$ is proportional to $exp(-L/A)$ wherein A corresponds with a maximum signal intensity recorded for a mass peak. Preferably, A corresponds with a mean or average signal intensity recorded for mass peaks.

According to an embodiment the prior probability distribution function $Pr(L)$ has a gamma, Poisson, Gaussian, exponential, normal or lognormal distribution. Preferably, the prior probability distribution function $Pr(L)$ has a distribution with an integral equal to one.

According to an embodiment the method further comprises determining, formulating or assigning a prior probability distribution function $Pr(k)$ for the overall response factor k of each component, molecule or analyte in the sample. Preferably, k includes one or more of the following: (i) digestion efficiency; (ii) relative product yield; (iii) losses in delivery; (iv) ionisation efficiency; (v) transmission efficiency; and (vi) detection efficiency. According to an embodiment the prior probability distribution function $Pr(k)$ is proportional to $exp(-k/k_0)$, where $k_0$ is a constant. Preferably, $k_0=1$.

According to an embodiment the prior probability distribution function $Pr(k)$ has a gamma, Poisson, Gaussian, exponential, normal or lognormal distribution. Preferably, the prior probability distribution function $Pr(k)$ has a distribution with an integral equal to one.

According to an embodiment the method further comprises determining, formulating or assigning a prior probability distribution function $Pr(h)$ for the relative amount of sample h of each component, molecule or analyte in each sample used in an analysis. Preferably, h includes one or more of the following: (i) amount of solvent added; and (ii) amount of material injected.

Preferably, the prior probability distribution function $Pr(h)$ is proportional to $exp(-h/h_0)$, where $h_0$ is a constant. Preferably, $h_0=1$.

According to an embodiment the prior probability distribution function $Pr(h)$ has a gamma, Poisson, Gaussian, exponential, normal or lognormal distribution. Preferably, the prior probability distribution function $Pr(h)$ has a distribution with an integral equal to one.

According to an embodiment the method further comprises determining, formulating or assigning a prior probability distribution function $Pr(G)$ for the noise contribution factor G assumed for observed signal intensities and/or applied to predicted signal intensities. Preferably, G includes one or more of the following: (i) ion statistical shot noise; and (ii) Electrospray ionisation droplet statistical shot noise.

The prior probability distribution function $Pr(G)$ is preferably proportional to $exp(-G/G_0)$, where $G_0$ is a constant. Preferably, $G_0=1$.

According to an embodiment the prior probability distribution function $Pr(G)$ has a gamma, Poisson, Gaussian, exponential, normal or lognormal distribution. Preferably, the prior probability distribution function $Pr(G)$ has a distribution with an integral equal to one.

According to an embodiment the method further comprises locating, determining, identifying or choosing one or more internal standards or references. Preferably, the one or more internal standards or references comprise one or more components, molecules or analytes which have substantially the same intensity, concentration or expression level in all of the samples.

The one or more internal standards or references may comprise one or more components, molecules or analytes added to each sample. The one or more internal standards or references may be endogenous or exogenous to the first sample and/or the second sample and/or further samples.

The method preferably further comprises applying or using a Markov Chain Monte Carlo predictive procedure or investigating iteratively using a Markov Chain Monte Carlo algorithm to determine likely values for the relative concentrations L of each component, molecule or analyte in each of the samples. Preferably, the Markov Chain Monte Carlo predictive procedure or algorithm is selected from the group consisting of: (i) Metropolis Hastings algorithm; (ii) Gibbs Sampling algorithm; (iii) Hamiltonian Monte Carlo algorithm; and (iv) Slice Sampling algorithm.

According to an embodiment the Markov Chain Monte Carlo predictive procedure or algorithm is used in conjunction with simulated annealing and/or nested sampling.

According to an embodiment the method further comprises predicting what would be observed for each mass peak intensity given probability distribution functions Pr(L) and/or Pr(k) and/or Pr(h) and/or Pr(G) and/or given the probability p of correct identification.

According to an embodiment the method further comprises comparing peak intensities that are predicted with those that are observed.

According to an embodiment the method further comprises adjusting the value of L or the probability distribution function Pr(L).

According to an embodiment the method further comprises adjusting the value of k or the probability distribution function Pr(k).

According to an embodiment the method further comprises adjusting the value of h or the probability distribution function Pr(h).

According to an embodiment the method further comprises adjusting the value of G or the probability distribution function Pr(G).

According to an embodiment the method further comprises predicting what would be observed for each mass peak intensity given the adjusted probability distribution functions Pr(L) and/or Pr(k) and/or Pr(h) and/or Pr(G) and/or given the probability p of correct identification.

The method preferably further comprises comparing peak intensities that are predicted with those that are observed.

According to an embodiment the method further comprises accepting or rejecting adjusted probability distribution functions. Preferably, the method further comprises repeating or terminating the cycle of adjusting probability distribution functions and/or predicting intensities and/or comparing predicted intensities with observed intensities.

Preferably, the method further comprises determining the ratios $L_{ij}$ of relative concentrations L of each component, molecule or analyte in each of the samples for every pair i,j of samples.

According to an embodiment the method further comprises continuing the Markov Chain Monte Carlo predictive procedure to determine more likely values for the relative concentrations L of each component, molecule or analyte in each of the samples and the ratios $L_{ij}$ of the relative concentrations L.

The number of determinations of the ratios $L_{ij}$ of the relative concentrations L is preferably pre-defined according to required accuracy of mean values.

The method preferably further comprises calculating mean values for the ratios $L_{ij}$ of the relative concentrations L of each component, molecule or analyte in each of the samples for every pair i,j of the samples.

According to an embodiment the method further comprises calculating standard deviations and/or relative standard deviations for the ratios $L_{ij}$ of the relative concentrations L of each component, molecule or analyte in each of the samples for every pair i,j of the samples.

According to an embodiment the first sample and/or the second sample and/or further samples comprise a plurality of different biopolymers, proteins, peptides, polypeptides, oligionucleotides, oligionucleosides, amino acids, carbohydrates, sugars, lipids, fatty acids, vitamins, hormones, portions or fragments of DNA, portions or fragments of CDNA, portions or fragments of RNA, portions or fragments of mRNA, portions or fragments of tRNA, polyclonal antibodies, monoclonal antibodies, ribonucleases, enzymes, metabolites, polysaccharides, phosphorolated peptides, phosphorolated proteins, glycopeptides, glycoproteins or steroids.

The first sample and/or the second sample and/or further samples may comprise at least 2, 5, 10, 20, 30, 40, 50, 60, 70, 80, 90, 100, 200, 300, 400, 500, 600, 700, 800, 900, 1000, 1500, 2000, 2500, 3000, 3500, 4000, 4500, or 5000 components, molecules or analytes having different identities or comprising different species.

The first sample and/or the second sample and/or further samples may comprise non-equimolar heterogeneous complex mixtures. Preferably, either: (i) the first sample is taken from a diseased organism and the second sample is taken from a non-diseased organism; (ii) the first sample is taken from a treated organism and the second sample is taken from a non-treated organism; or (iii) the first sample is taken from a mutant organism and the second sample is taken from a wild type organism.

According to an embodiment the method further comprises identifying components, molecules or analytes in the first sample and/or the second sample and/or further samples The components, molecules or analytes in the first sample and/or the second sample and/or further samples are preferably only identified if the intensity of the components, molecules or analytes in the first sample differs from the intensity of the components, molecules or analytes in the second sample and/or further samples by more than a predetermined amount.

The components, molecules or analytes in the first sample and/or the second sample and/or further samples may only identified if the average intensity of a plurality of different components, molecules or analytes in the first sample differs from the average intensity of a plurality of different components, molecules or analytes in the second sample and/or further samples by more than a predetermined amount.

The predetermined amount is preferably selected from the group consisting of: (i) 1%; (ii) 2%; (iii) 5%; (iv) 10%; (v) 20%; (vi) 50%; (vii) 100%; (viii) 150%; (ix) 200%; (x) 250%; (xi) 300%; (xii) 350%; (xiii) 400%; (xiv) 450%; (xv) 500%; (xvi) 1000%; (xvii) 5000%; and (xviii) 10000%.

The mass or mass to charge ratio of molecules, components or analytes and/or peptide digest products and/or fragment, daughter or product ions are preferably mass analysed by either: (i) a Fourier Transform ("FT") mass spectrometer; (ii) a Fourier Transform Ion Cyclotron Resonance ("FTICR") mass spectrometer; (iii) a Time of Flight ("TOF") mass spectrometer; (iv) an orthogonal acceleration Time of Flight ("oaTOF") mass spectrometer; (v) a magnetic sector mass spectrometer; (vi) a quadrupole mass analyser; (vii) an ion trap mass analyser; and (viii) a Fourier Transform orbitrap, an electrostatic Ion Cyclotron Resonance mass spectrometer or an electrostatic Fourier Transform mass spectrometer.

The first sample and/or the second sample and/or further samples are preferably ionised by an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; and (xvi) a Nickel-63 radioactive ion source.

According to an aspect of the present invention there is provided a mass spectrometer comprising means arranged to probabilistically determine or quantify the relative intensity, concentration or expression level of a component, molecule or analyte in a first sample relative to the intensity, concentration or expression level of a component, molecule or analyte in a second sample.

The mass spectrometer preferably further comprises a liquid chromatograph.

According to an embodiment the mass spectrometer further comprises one or mass filters and/or one or more mass analysers. The one or more mass filters and the one or more mass analysers are preferably selected from the group consisting of: (i) an orthogonal acceleration Time of Flight mass analyser; (ii) an axial acceleration Time of Flight mass analyser; (iii) a Paul 3D quadrupole ion trap mass analyser; (iv) a 2D or linear quadrupole ion trap mass analyser; (v) a Fourier Transform Ion Cyclotron Resonance mass analyser; (vi) a magnetic sector mass analyser; (vii) a quadrupole mass analyser; and (viii) a Penning trap mass analyser.

The mass spectrometer preferably further comprises an ion source. The ion source may comprise a pulsed ion source or a continuous ion source. The ion source may be selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; and (xvi) a Nickel-63 radioactive ion source.

According to an aspect of the present invention there is provided a method of relatively quantifying one or more molecular species among several samples, the method comprising:

dividing each sample into multiple replicate samples;

for each of the replicate samples obtaining a signal for each of several tentatively identified digestion products of the molecular species in question, wherein the signal is proportional to the concentration of the parent species subject to random noise;

obtaining or assigning probabilities that each tentative identification is correct;

assigning a prior probability distribution function for the relative amount L of each molecular species in each sample;

assigning a prior probability distribution function for the relative amount k of digestion product produced from each molecular species;

assigning a prior probability distribution function for the relative amount h of sample for each replicate sample;

assigning a prior probability distribution function for the noise level G in each sample;

choosing an internal standard wherein the concentration of the internal standard is known to be the same in all of the replicate samples;

updating the probability distribution for the relative amount L of each molecular species in each sample;

obtaining samples according to the probability distribution for the relative amount L of each molecular species in each sample of a monotonic function of the ratios $L\_i$ to $L\_j$ for every distinct pair i,j of the replicate samples; and calculating a mean value and standard deviation of the function for each of the pairs.

According to an aspect of the present invention there is provided a method of mass spectrometry comprising:

providing a first sample comprising a first mixture of components, molecules or analytes;

providing a second different sample comprising a second mixture of components, molecules or analytes; and determining or quantifying the relative intensity, concentration or expression level of a component, molecule or analyte in said first sample relative to the intensity, concentration or expression level of a component, molecule or analyte in said second sample.

According to an aspect of the present invention there is provided a mass spectrometer comprising means arranged to determine or quantify the relative intensity, concentration or expression level of a component, molecule or analyte in a first sample relative to the intensity, concentration or expression level of a component, molecule or analyte in a second sample.

The preferred embodiment preferably uses a forward modelling algorithm to average over the contribution of unknown ionisation and digestion efficiencies to the measured ion count. The measured ion count of a peptide can be expressed as being proportional to the product of its concentration in the original sample and a factor relating to its ionisation and digestion efficiencies. Values of concentration and digestion/ionisation efficiency are preferably explored for each peptide and likelihoods are preferably calculated for each result using supplied probabilities of the compounds present in the samples. The likelihood calculation preferably does not advantageously require missing data to be interpolated or otherwise filled in. This is in contrast to conventional approaches.

A further feature of the exploration according to the preferred embodiment is that assignments to data can be switched on or off such that the presence of outliers or outlying data may be investigated. Relative concentrations of proteins or peptides in each sample can then be calculated and a percentage confidence interval given using the results of the probabilistic exploration.

Mass spectral data and microarray data present different challenges. The preferred embodiment is particularly concerned with data which exhibits underlying Poisson noise (counting statistics). This is particularly appropriate when an analytical instrument determines the abundance of daughter compounds (e.g. peptides or peptide digest products) and reports a number of events (e.g. intensity). The events may, for example, relate to the number of ion arrivals in a quadrupole Time of Flight mass spectrometer. However, this is not appropriate to continuous quantities such as the colour/brightness of a microarray spot.

In its simplest form, the preferred algorithm as implemented in the method and apparatus according to the preferred embodiment may be considered as being directed to solving a problem where there are two unknown numbers A and B and it is desired to determine the ratio of B/A. Samples of A ($A_1, A_2 \ldots A_N$) and B ($B_1, B_2 \ldots B_M$) are provided. In general, N and M are not equal although the cases N=1 and M=1 are permitted. The samples of A and B can either be considered as "Good" or "Bad" and each sample may be considered as coming with a probability e.g. $Pr(A_3$ is Good). A "Good" sample of A will be close to A in some mathematically well defined sense. "Bad" samples of A could be almost anything. The same applies to B.

According to the preferred embodiment it is desired to infer the ratio B/A given only this information, and also to provide an uncertainty estimate for the ratio. In the preferred embodiment, the numbers A and B are proportional to concentrations of peptides in solution as measured by a mass spectrometer. The following example may be considered:

| Measurement | Prob |
|---|---|
| Sample A | |
| 100 | 0.91 |
| 96 | 0.89 |
| 107 | 0.92 |
| 111 | 0.98 |
| 98 | 0.91 |
| 104 | 0.97 |
| 111 | 0.83 |
| 104 | 0.88 |
| 246 | 0.89 |
| Sample B | |
| 510 | 0.87 |
| 487 | 0.96 |
| 97 | 0.63 |
| 530 | 0.78 |

From the above data it may be considered that A equals 100 and that B equals 500 is plausible if the last sample of A and the third sample of B are considered as being "bad" and hence are rejected as being outliers. The preferred embodiment does not however immediately reject data which may initially appear to be spurious.

The ratio B/A as determined by the preferred embodiment and a corresponding uncertainty estimate is determined to be 5.1±0.1.

The preferred embodiment can be considered from a different perspective and can be considered as addressing a second related question. This problem can be considered to be that there are 2+K unknown numbers A, B, $k_1, k_2 \ldots k_K$ and that some of the 2*K possible products are provided or known:

| $A * k_1$ | $A * k_2$ | ... | $A * k_K$ |
|---|---|---|---|
| $B * k_1$ | $B * k_2$ | ... | $B * k_K$ |

It can be considered that any number of samples of any of these products are provided. Samples can either be considered to be "Good" or "Bad" in the same sense as above, and each sample again comes with an associated probability. The problem is again to estimate B/A and provide an uncertainty estimate.

According to the preferred embodiment the numbers A and B are proportional to concentrations of intact proteins in solution prior to digestion, and the other unknowns $k_i$ are related to the digestion and ionisation characteristics of the proteins tryptic peptides. The coefficients $k_i$ are not of particular interest and it is not necessary actually to calculate them.

The preferred embodiment relates to a method and apparatus which incorporates an algorithm designed to quantify changes in abundance of an analyte compound across several physical samples containing the analyte or its products and at least one internal standard compound. Any number of replicate measurements may be available from each sample, and the data may be noisy and generally also incomplete. It is known from the outset that there is a probability of incorrect assignment of data and that some assignments are more likely to be correct than others.

The preferred embodiment relates to the application of a novel mathematical model of the data and to using Markov chain Monte Carlo techniques to explore the space of model parameters in such a way that changes in abundance along with associated uncertainties can be measured and determined.

Standard statistical techniques such as pairwise t-tests and ANOVA cannot be applied in situations where the number of measurements in each sample is different, when measurements are missing, where assignments of data are ambiguous, where measurements are experimentally correlated or where the number of measurements is very small.

As will be appreciated by those skilled in the art, in the real world experimental data is often noisy and incomplete and hence it is apparent that conventional known techniques are of limited use in being able to process and analyse noisy and incomplete experimental data.

A particular advantageous aspect of the preferred embodiment is that a normalisation step does not need to be performed as a separate step in order to determine the relative concentration of a particular analyte present in two or more separate samples.

Multiple experiments are preferably performed and an analyte for which the concentration is the same in all experiments is preferably used as an internal standard. The preferred embodiment allows for daughter compounds (e.g. peptides) which are associated probabilistically with parents (e.g. proteins). This is particularly useful when daughters are enzymatic digest products of proteins and wherein peptide identification information comes from tandem mass spectrometry.

The preferred embodiment also deals transparently with missing data. Conventional approaches, by contrast, are particularly problematic and prone to error when data is missing.

The preferred embodiment relates to a probabilistic or Bayesian method of measuring differences in the relative concentration of a particular analyte present in multiple different samples.

The preferred embodiment is particularly advantageous in being able accurately to quantify analytes present in samples even though the experimental data may be less than perfect. The data may, for example, suffer from an unknown gain and/or there may be other global or poorly understood sources of noise. The concentration of each analyte in the original samples may be represented in the data by one or more compounds. These compounds preferably comprise digestion product/fragments which shall be referred to hereinafter as daughters.

For each sample several replicate experiments are preferably performed i.e. the sample is divided up into a number of sub-samples and each sub-sample may be separately analysed. As will be appreciated, running the preferred procedures on multiple replicate samples helps to improve the accuracy of the quantification steps according to the preferred embodiment. However, it is not essential that samples be divided into a number of replicate samples and that each replicate sample be analysed separately.

It is contemplated that different (and unknown) quantities of a sample may be used in each replicate experiment so that there may be significant variations in the data among the replicate experiments.

The identity of each peptide may be in question, but according to the preferred embodiment a probability $P_{ij}=Pr$ (Protein is analyte j given data associated with peptide i) is either available or is set to some uniform value. This information may, for example, come from the analysis of fragments of peptides by tandem mass spectrometry (MSMS) wherein peptide digest products are fragmented in a collision or fragmentation cell and the resulting fragment, daughter or product ions are mass analysed.

Some peptides may not have complete coverage across all experiments for reasons other than low concentration. Such reasons may be practical considerations. For example, a number of peptides with a similar mass to charge ratio may elute from the liquid chromatograph at a similar time making identification difficult.

The preferred embodiment enables an output to be generated which may comprise ratios of concentration for each analyte between pairs of conditions with associated uncertainties, the probability that each ratio exceeds one, a full posterior probability distribution for each ratio, or other desired statistics.

The preferred method assumes that the ideal measured intensity of each peptide in the mass spectral data is proportional to the concentration of the corresponding parent protein, that the measured intensities are inherently subject to at least Poisson noise (counting statistics), and that there exists at least one measured peptide which can be assumed to be at the same concentration in each experiment for each sample (this will be referred to hereinafter as an "internal standard").

The preferred method depends on constructing a model of the data taking into account the problems and requirements described above.

The underlying data $D_U$ for each peptide (before noise and gain) is assumed to be given by:

$$D_U = Lhk \qquad (1)$$

where L is the concentration of protein present in a sample, h expresses how much sample (or what fraction of the sample) was used in a particular replicate experiment and k is a coefficient which expresses the efficiency with which a peptide is produced from the corresponding protein ion and also how efficiently the mass spectrometer observes the peptide ion.

The actual observed data $D_O$ is assumed to be subject to Poisson noise and an unknown gain G to allow for global scaling of the noise level. For a particular peptide ion, the probability of observing $D_O$ given a particular set of model parameters L, k and h is:

$$Pr(D_O|L,k,h) = Pr(D_O|D_U)p + Pr(D_O|B)(1-p) \qquad (2)$$

where:

$$Pr(D_0|D_U) = \frac{1}{G}\frac{\exp(-D_U/G)(D_U^{D_O}/G)}{\Gamma(D_O/G+1)} \qquad (3)$$

and is a modified Poisson distribution which captures the degree of agreement of the predicted theoretical data with the actual experimentally observed data.

The quantity in Equation 2 will be referred to hereinafter as the likelihood. With reference to Equations 2 and 3 above, the Gamma function $\Gamma(x)$ is a commonly used special function, p is the probability that the parent analyte is correctly assigned and $Pr(D_0|B)$ is the background probability of observing a particular datum $D_0$ given an incorrect parent assignment. According to the preferred embodiment:

$$Pr(D_O|B) = \frac{1}{\Lambda}\exp\left(-\frac{D_O}{\Lambda}\right) \qquad (4)$$

Equation 4 reflects the fact that data attached to an incorrect assignment could be almost anything roughly consistent with the overall scale of the data $\Lambda$. In a preferred embodiment, $\Lambda$ is taken to be the size of the largest datum. In a less preferred embodiment, $\Lambda$ is taken to be a probability weighted average over all data. Should the result of the probability function as detailed in Equation 4 be larger and thus more significant in calculating the likelihood (Equation 2) than the result of Equation 3, then the assignment can be considered incorrect.

In order to complete the probabilistic formulation of the problem, it is necessary to specify prior probability distributions for each of the parameters L, h, k and G. The prior probability distributions are denoted Pr(L), Pr(h) etc. The prior probability distributions encapsulate what is known about the parameters before the data is examined, ensuring that unrealistic values are not investigated. In the preferred embodiment an exponential form for the prior probability distributions for parameters L, h, k and G is preferably used. For example:

$$Pr(L|D) = \frac{1}{L_0}\exp(-L/L_0) \qquad (5)$$

There are various different possible prescriptions for choosing $L_0$ in Equation 5. According to the preferred embodiment $L_0$ is set as being $\Lambda$, $k_0$ is set as being 1, $h_0$ is set as being 1 and $G_0$ is also set as being 1.

With these parameters defined, particular choices of prior probability distributions can be linked with the calculated likelihood for given values of L, h and k to give the joint probability distribution, which can be expressed as:

$$Pr(L, h, k, G, \text{Data}) = Pr(L)Pr(h)Pr(k)Pr(G)\prod_{Data} Pr(D_O|L, h, k) \qquad (6)$$

where L, h and k are vectors on the LHS of the above expression. The dimension of the vector L is the number of samples multiplied by the number of analytes. The dimension of the vector h is the number of experiments. The dimension of the vector k is the number of daughters (e.g. peptides). According, the total number of model parameters (including the gain and ignoring the internal standard) equals (the number of samples times the number of analytes) plus (the number of experiments) plus (the number of daughters) plus 1.

The joint probability distribution as given in Equation 6 is therefore a high dimensional function. The quantity of interest, however, is preferably the set of ratios of elements of the vector L and the corresponding set of uncertainties, relating to a single protein or peptide in multiple samples. It is preferred not to locate the single vector L which maximises the joint probability, but to obtain probability distributions for ratios of elements of L. An example would be Pr(L2/L1, Data). Such probability distributions are often asymmetrical, making the associated uncertainties difficult to express. Thus it is preferred to express the probability distributions for monotonic functions of ratios of elements of L, for instance natural logarithms of ratios of elements of L. These distributions allow estimates of the ratios to be quoted with associated uncertainties or any other desired statistics.

Appropriate methods to perform this exploration are known to those skilled in the art. General tools exist, for example, for solving this kind of problem including, for example, the publicly available inference engine BayeSys®.

An approximation may preferably be made to the full joint probability as detailed in Equation 6 above to bring about an increase in the speed of exploration. For each peptide, there is (at most) one contribution to the product in the joint probability (Equation 6) from each experiment.
These contributions have two terms each. The approximation preferably keeps only four terms per protein in the fully expanded joint probability. These four terms correspond to: (i) peptides assigned correctly in all experiments; (ii) peptides assigned correctly in all but least probable experiment (lowest value of p); (iii) peptides assigned incorrectly in all but strongest experiment (highest value of p); and (iv) peptides assigned incorrectly in all experiments.

In practice, however, even using powerful techniques such as applying Markov Chain Monte Carlo algorithms and simulated annealing, the solution to these problems can still become very slow when a large numbers of analytes is involved.

The preferred embodiment enables the exploration to proceed more efficiently by preferably analytically reducing the dimensionality of the posterior probability distribution (Equation 6) by removing all components of the vector k thus leaving one less parameter to explore and thus saving computational power, in a procedure known as marginalisation. This is possible as it is unnecessary to record the magnitude of the vector k.

Marginalisation is a process wherein both sides of the joint probability function (Equation 6) are integrated with respect to one of the vectors. In a preferred embodiment, marginalisation proceeds by the integration of the joint probability function with respect to k. In a less preferred embodiment, marginalisation may proceed by the integration of the joint probability function with respect to h.

In a less preferred embodiment, a further integration may be performed, such that k and h may both be removed from the joint probability function. The second integration in such a method is, however, often difficult (and sometimes impossible), as the first integral may not be a true function.

BRIEF DESCRIPTION OF THE DRAWINGS

Various embodiments of the present invention will now be described, by way of example only, and with reference to the accompanying drawings in which:

FIG. 1 shows some simulated noisy data where measurements for some analytes are not available; and FIG. 2 shows the actual relationship between sample quality and analyte expression and the relationship as determined according to the preferred embodiment.

DETAILED DESCRIPTION OF THE PREFERRED EMBODIMENTS

A preferred embodiment of the present invention will now be described. FIG. 1 shows simulated data with numbers produced using a random number generator. Four samples were considered and two replicate experiments were modelled for each sample. Accordingly, a total of eight experiments were performed. The actual, underlying or true relationships or ratios between the sample quantities h1-h8 and between the analyte expressions L1-L4 are shown in FIG. 2. FIG. 2 also shows the experimentally determined relationships or ratios as reconstructed according to the preferred embodiment from the noisy and incomplete data as shown in FIG. 1.

It is apparent from FIG. 1 that in the sixth experiment no data was modelled as being present or obtained for the internal standard or invariant ions. However, nonetheless as can be see from FIG. 2 the ratio h6/h1 has still been recovered successfully despite the lack of any internal standard in this experiment by the method of the preferred embodiment.

It is to be noted that all of the sample ratios were successfully recovered and are shown in FIG. 2 consistent within the reported uncertainties. This would not be possible using conventional techniques.

A number of further modifications to the preferred embodiment are contemplated. According to a modification the Poisson distribution given in Equation 3 above may be replaced by a Gaussian approximation to a Poisson distribution.

According to another embodiment the exponential prior probability distribution function as presented in Equation 4 above may be replaced by a gamma distribution for any of the parameters G,L,h or k. For example, according to an embodiment:

$$Pr(L \mid D) = \frac{L^{a-1}\exp(-L/t)}{\text{Gamma}(a)t^a} \qquad (7)$$

According to a further embodiment, the exponential prior probability distribution function as given in Equation 3 above may be replaced by a normal distribution for any of the parameters G, L, h or k. For example:

$$Pr(L \mid D) = \frac{1}{\sigma\sqrt{2\pi}}\exp\left(-\frac{(L-\mu)^2}{2\sigma^2}\right) \qquad (8)$$

The exponential prior probability distribution function as given in Equation 3 may according to another embodiment be replaced by a lognormal distribution for any of the parameters G, L, h or k. For example:

$$Pr(L \mid D) = \frac{1}{SL\sqrt{2\pi}}\exp\left(-\frac{(\ln L - M)^2}{2S^2}\right) \qquad (9)$$

According to an embodiment the value $L_0$ in Equation 3 above is set to the average datum size.

It is contemplated that a dimension could be removed from the model. According to such an embodiment, L may be multiplied by a constant and k could be divided by the same constant without changing the likelihood (Equation 2). A constraint could be added such as:

$$\prod_i h_i = 1$$

and the dependence on h could be recast in hyperbolic coordinates. This describes an alternative method of simplifying the probability distribution to marginalisation. Rather than integrating a value out of the equation in the case of marginalisation, a limit could instead be imposed on its possible values, such that there is less "space" for the algorithm to explore. To understand the concept of "space" a graph of $h_2$ axis over $h_1$ axis can be considered. If there is no limit imposed on values of h, then the algorithm must explore all positive values—zero to infinity—for $h_1$ and likewise for $h_2$, i.e. the entire positive region of the graph. By declaring the product of $h_1h_2=1$, the space that the algorithm needs to explore is limited to a single hyperbolic line on this graph (h2=1/h1, y=1/x). This leaves the values of h with some flexibility, so is a better approximation than simply assigning h1=1. This imposition can be made since the likelihood will remain the same if the value of k is altered accordingly.

According to another embodiment marginalisation may proceed by integrating over h instead of k.

As discussed above, since according to the preferred embodiment the values of L and Data are the only ones of particular interest, then all other values (i.e. G, h, k) in the joint probability function (See Equation 6 above) can be considered as being nuisance parameters i.e. parameter required for the calculation but otherwise unnecessary for the output. One of these values can be removed from the joint probability function by integrating both sides with respect to this value. For instance, to remove k, it is necessary to integrate with respect to k, giving:

$$Pr(L, h, G, \text{Data}) = \int \left( Pr(L)Pr(h)Pr(k)Pr(G) \prod_{Data} Pr(D_O | L, h, k) \right) dk \quad (10)$$

thus leaving the algorithm one less parameter to explore, and saving computational time. The result of such an integral is unlikely to be a function, so further integration is unlikely to be possible. It is not usually possible to integrate the function with respect to G, the program usually doing so with respect to h or k.

The analytes could according to an embodiment be processed one at a time along with the internal standard rather than modelling the whole data set at once.

According to an embodiment the preferred embodiment may tackle the problem in two parts. Firstly, h may be inferred and then L may be inferred given the inference about h.

According to an embodiment there may not be any daughters (e.g. peptides) i.e. it may be possible to quantify directly on the analytes, or it may not be possible to make the associations described above and treat each daughter as a separate analyte.

A further embodiment is contemplated wherein different approximations may be made to the joint probability distribution given in Equation 6 above. For example, up to six terms or eight terms may be kept, or all terms may be retained. It is also contemplated that the joint probability distribution could be explored without marginalisation.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
   providing a first sample comprising a first mixture of components, molecules or analytes;
   providing a second different sample comprising a second mixture of components, molecules or analytes; and
   probabilistically determining or quantifying the relative intensity, concentration or expression level of a component, molecule or analyte in said first sample relative to the intensity, concentration or expression level of a component, molecule or analyte in said second sample;
   wherein said first sample and said second sample comprise a plurality of different biopolymers, proteins, protein digest products, peptides, fragments of peptides, polypeptides, oligionucleotides, oligionucleosides, amino acids, carbohydrates, sugars, lipids, fatty acids, vitamins, hormones, portions or fragments of DNA, portions or fragments of cDNA, portions or fragments of RNA, portions or fragments of mRNA, portions or fragments of tRNA, polyclonal antibodies, monoclonal antibodies, ribonucleases, enzymes, metabolites, polysaccharides, phosphorolated peptides, phosphorolated proteins, glycopeptides, glycoproteins or steroids.

2. A method as claimed in claim 1, further comprising providing a plurality of further samples each comprising a mixture of components, molecules or analytes.

3. A method as claimed in claim 1, further comprising:
   digesting said first mixture of components, molecules or analytes; or
   digesting said second mixture of components, molecules or analytes; or
   digesting further mixtures of components, molecules or analytes.

4. A method as claimed in claim 1, further comprising:
   dividing said first sample into one or more first replicate samples; or
   dividing said second sample into one or more second replicate samples; or
   dividing further samples into one or more further replicate samples; or
   dividing said first complex mixture into one or more first replicate samples; or
   dividing said second complex mixture into one or more second replicate samples; or
   dividing said further complex mixtures into one or more further replicate samples.

5. A method as claimed in claim 1, further comprising:
   separating components, analytes or molecules in said first sample by means of a separation process; or
   separating components, analytes or molecules in said second sample by means of a separation process; or
   separating components, analytes or molecules in further samples by means of a separation process; or
   separating components, analytes or molecules in first replicate samples by means of a separation process; or
   separating components, analytes or molecules in second replicate samples by means of a separation process; or
   separating components, analytes or molecules in further replicate samples by means of a separation process.

6. A method as claimed in claim 5, wherein said separation process comprises liquid chromatography.

7. A method as claimed in claim 1, further comprising:
mass analysing components, analytes or molecules in said first sample; or
mass analysing components, analytes or molecules in said second sample; or
mass analysing components, analytes or molecules in further samples; or
mass analysing components, analytes or molecules in first replicate samples; or
mass analysing components, analytes or molecules in second replicate samples; or
mass analysing components, analytes or molecules in further replicate samples;
wherein said step of mass analysing components, analytes or molecules further comprises producing mass spectral data comprising a plurality of mass peaks.

8. A method as claimed in claim 7, further comprising clustering mass peaks from said first sample or said second sample or further samples or from first replicate sample or second replicate sample or further replicate samples.

9. A method as claimed in claim 8, wherein components, analytes or molecules are recognised or identified on the basis of chromatographic retention time.

10. A method as claimed in claim 8, further comprising:
identifying or recognising components, molecules or analytes in said first sample on the basis of fragment, daughter or product ions; or
identifying or recognising components, molecules or analytes in said second sample on the basis of fragment, daughter or product ions; or
identifying or recognising components, molecules or analytes in further samples on the basis of fragment, daughter or product ions.

11. A method as claimed in claim 1, further comprising determining, formulating or assigning a prior probability distribution function $Pr(L)$ for the relative amount or concentration L of components, molecules or analytes present in each sample.

12. A method as claimed in claim 1, further comprising determining, formulating or assigning a prior probability distribution function $Pr(k)$ for the overall response factor k of each component, molecule or analyte in said sample.

13. A method as claimed in claim 12, wherein k includes one or more of the following: (i) digestion efficiency; (ii) relative product yield; (iii) losses in delivery; (iv) ionisation efficiency; (v) transmission efficiency; and (vi) detection efficiency.

14. A method as claimed in claim 1, further comprising determining, formulating or assigning a prior probability distribution function $Pr(h)$ for the relative amount of sample h of each component, molecule or analyte in each sample used in an analysis.

15. A method as claimed in claim 1, further comprising determining, formulating or assigning a prior probability distribution function $Pr(G)$ for the noise contribution factor G assumed for observed signal intensities or applied to predicted signal intensities.

16. A method as claimed in claim 1, further comprising locating, determining, identifying or choosing one or more internal standards or references.

17. A method as claimed in claim 1, further comprising predicting what would be observed for each mass peak intensity given probability distribution functions $Pr(L)$ or $Pr(k)$ or $Pr(h)$ or $Pr(G)$ or given the probability p of correct identification.

18. A method as claimed in claim 17, further comprising comparing peak intensities that are predicted with those that are observed.

19. A method as claimed in claim 17, further comprising adjusting the value of L or the probability distribution function $Pr(L)$; or adjusting the value of k or the probability distribution function $Pr(k)$; or adjusting the value of h or the probability distribution function $Pr(h)$; or adjusting the value of G or the probability distribution function $Pr(G)$.

20. A method as claimed in claim 17, further comprising predicting what would be observed for each mass peak intensity given said adjusted probability distribution functions $Pr(L)$ or $Pr(k)$ or $Pr(h)$ or $Pr(G)$ or given the probability p of correct identification.

21. A method as claimed in claim 20, further comprising accepting or rejecting adjusted probability distribution functions.

22. A method as claimed in claim 21, further comprising determining the ratios $L_{ij}$ of relative concentrations L of each component, molecule or analyte in each of said samples for every pair i,j of samples.

23. A method as claimed in claim 1, wherein either: (i) said first sample is taken from a diseased organism and said second sample is taken from a non-diseased organism; (ii) said first sample is taken from a treated organism and said second sample is taken from a non-treated organism; or (iii) said first sample is taken from a mutant organism and said second sample is taken from a wild type organism.

24. A method as claimed in claim 1, further comprising identifying components, molecules or analytes in said first sample or said second sample or further samples.

25. A method as claimed in claim 1, wherein said components, molecules or analytes in said first sample or said second sample are only identified if the intensity of said components, molecules or analytes in said first sample differs from the intensity of said components, molecules or analytes in said second sample by more than a predetermined amount.

26. A method as claimed in claim 1, wherein said components, molecules or analytes in said first sample or said second sample are only identified if the average intensity of a plurality of different components, molecules or analytes in said first sample differs from the average intensity of a plurality of different components, molecules or analytes in said second sample by more than a predetermined amount.

* * * * *